United States Patent [19]

Galbraith et al.

[11] Patent Number: 4,512,659
[45] Date of Patent: Apr. 23, 1985

[54] APPARATUS FOR CALIBRATING A SURFACE SCANNER

[75] Inventors: Lee K. Galbraith; Jiri Pecen, both of Mountain View, Calif.

[73] Assignee: Tencor Instruments, Mountain View, Calif.

[21] Appl. No.: 522,632

[22] Filed: Aug. 10, 1983

[51] Int. Cl.³ .............................................. G01J 1/02
[52] U.S. Cl. ..................................... 356/243; 356/237
[58] Field of Search ................ 256/237, 243; 250/563, 250/572; 29/574

[56] References Cited

U.S. PATENT DOCUMENTS 3,963,354  6/1976  Feldman et al. ................. 250/572 X
4,386,850  6/1983  Leahy ............................. 356/237 X

OTHER PUBLICATIONS

Gaston, "Standard Wafer for Intensity and Focus Testing", *IBM Tech. Discl. Bull.*, vol. 24, No. 11A, pp. 5587–5589, Apr. 1982.

Primary Examiner—Davis L. Willis
Assistant Examiner—Matthew W. Koren
Attorney, Agent, or Firm—Thomas Schneck

[57] ABSTRACT

A test device for calibrating an optical scanner wherein microscopic patterns of light scattering elements simulate the scattering of light from particles or flaws of different sizes. Simulation of different particles sizes is achieved by means of clusters or arrays of these light scattering elements having different areawise densities. Patterns of such clusters or arrays are disposed on a surface with intervening spaces where a random assortment of foreign particles may be expected. In this manner, the foreign particles may be directly compared to a test pattern. The test surface may be a semiconductor wafer having a thin, inert coating with openings therein forming the light scattering elements. The openings may be made by photolithographic techniques, i.e., masking and etching, so that various patterns on a surface may be all created simultaneously by the same process.

6 Claims, 3 Drawing Figures

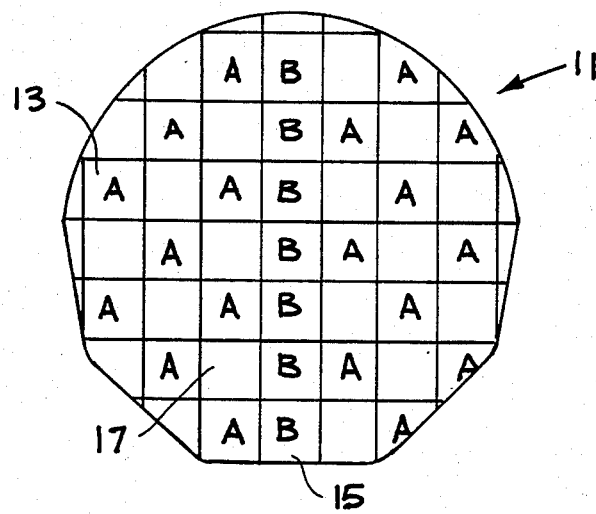
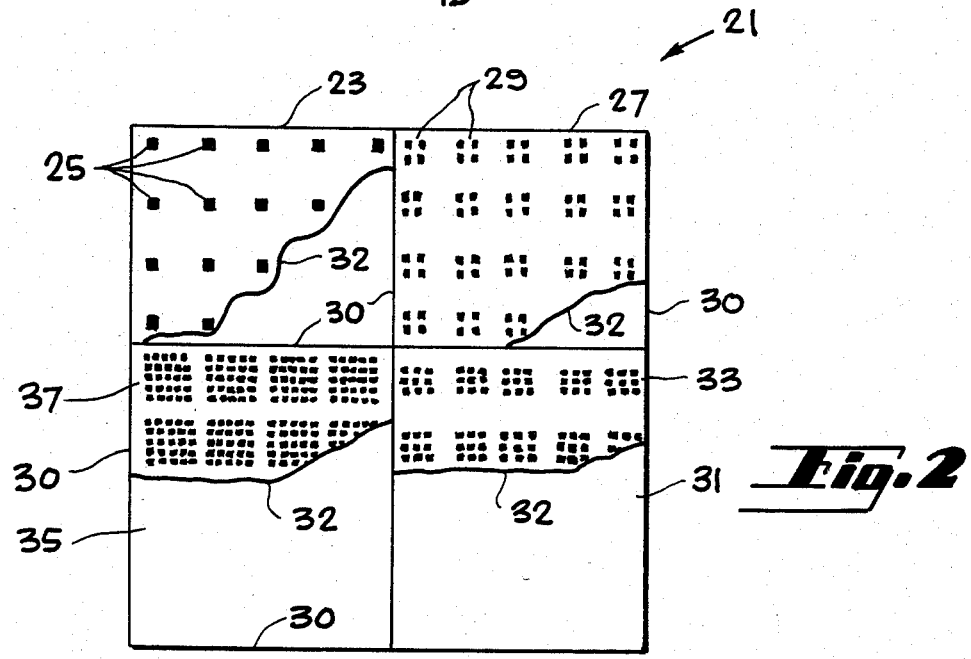
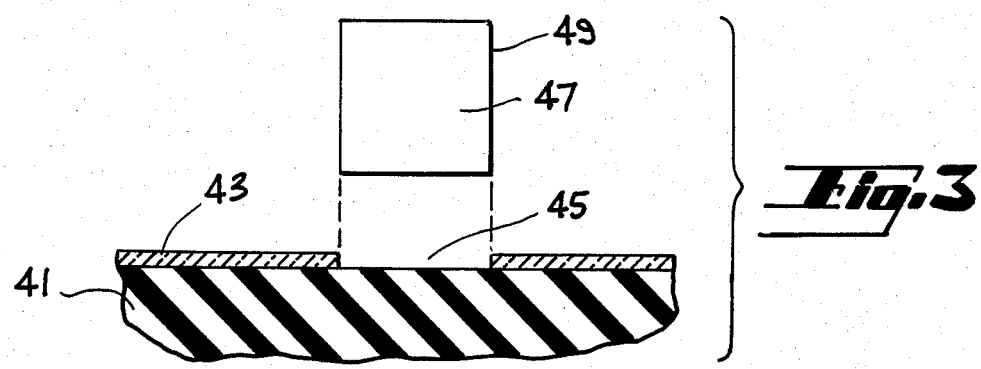

APPARATUS FOR CALIBRATING A SURFACE SCANNER

DESCRIPTION

1. Field of the Invention

The invention relates to testing of optical scanners and more particularly to a method and apparatus of calibrating microscopic flaw or microscopic contaminant detectors of the scanning type, particularly for use in semiconductor wafer inspection.

2. Background Art

Various types of optical scanners are used for flaw detection in materials, particularly surfaces and for detection of foreign matter on such surfaces. Foreign matter may be in the form of particles, such as dust or dirt.

U.S. Pat. No. 4,378,159 to Galbraith describes a surface scanner of the prior art. In such scanners the instrument sensitivity may be specified by factory testing. However, a user is never sure whether the factory specifications are still valid for a particular instrument or whether such specifications are applicable to all portions of a test surface.

In microscope calibration and testing, a procedure for determining instrument sensitivity involves disposing a number of microscopic spheres of known size on a surface. If the spheres can be observed at a certain power, the sensitivity of the instrument is known. The same technique has been used for surface scanners. A problem with spheres is that their position cannot be accurately controlled. Because the spheres are so small, there are difficulties in handling and dispensing them. However, a benefit of using spheres is that they can be made extremely small with uniform size and they have good light scattering properties. In balance, it is desireable to have a method and means for calibrating optical scanners which does not have the handling problems of spheres, yet has the dimensional uniformity and light scattering properties of spheres. This is the object of the present invention.

Disclosure of Invention

The above object has been achieved by creation of a surface having a plurality of fixed light scattering element patterns. The patterns may be formed by a relief pattern on a semiconductor substrate. The light scattering elements may be depressions or openings in the surface, as well as bumps or ridges. The elements may be a combination of depressions and bumps. The patterns have spaces therebetween so that scattering from the patterns can be compared to light scattering from the spaces where a random assortment of foreign particles may be expected.

Each pattern has a characteristic scattering cross section which gives rise to a sensitivity or resolution for the instrument. The cross section for the patterns is established by the areawise density of microscopic light scattering elements therein. For example, a high concentration of light scattering elements causes an aggregated high amount of scattering, simulating light which would be scattered from relatively large particles, while a low concentration of light scattering elements causes a lesser amount of scattering, simulating light scattered from relatively small particles.

A scanning beam is swept over the surface and light reflected and scattered from the surface is collected in a detector having an output of electrical signals corresponding to the amount of collected light. The electrical signals are synchronized to the position of a scanning beam and displayed on a screen so that the various patterns can be compared with particulate or foreign matter in the spaces.

The patterns may be disposed over the entire surface of a wafer or other surface so that the sensitivity of the instrument over the entire surface may be checked. Since scanning beams frequently scan in an arc, some surface regions may exhibit one sensitivity, while other regions exhibit another sensitivity.

BRIEF DESCRIPTION OF THE DRAWINGS

FIG. 1 is a top plan view of a calibration device in accord with the present invention with a plurality of patterned regions labeled A and B.

FIG. 2 is a magnification of one of the A patterns illustrated in FIG. 1.

FIG. 3 is a side sectional detail showing the method of formation of depressions in a surface of the kind illustrated in FIG. 1 for formation of light scattering elements.

BEST MODE FOR CARRYING OUT THE INVENTION

The present invention involves disposing test patterns of scattering elements on a surface such that light scattered from these elements simulates amounts of light which would be scattered from particles or defects, such as cracks. By providing different areawise densities of light scattering elements, scattered light is aggregated such that a cluster of elements having a low areawise density of the scattering elements simulates small particles and defects, while a cluster of elements having a large areawise density of light scattering elements simulates larger particles and flaws. In each case simulation is achieved because the light scattering cross section of a cluster equals the light scattering cross section of particles of a particular size.

With reference to FIG. 1, a wafer 11 may be seen having a surface divided into regions labeled A and B. The regions are squares, but other shapes may be used. The squares without any letter are spaces which are left clear of any patterns of light scattering elements. One type of representative pattern, A, may be found in square 13, while a second type of pattern, B, may be found in square 15. A space is seen in square 17. The group of A patterns appears as a checkerboard, while the group of B patterns appears as a stripe intersecting the checkerboard. The reason for this arrangement of patterns is so that an entire surface may be tested. This is important since beam scanning instruments usually use mirrors to cause sweeping of a beam across a surface. Each sweep is an arc, with the arc length being slightly different for different points on the surface. Thus, the center of a surface may have one resolution, while another resolution exists at the outermost edges of the surface. It is important to provide spaces between patterns so that actual flaws or particulates may be compared with the different patterns of light scattering elements.

With reference to FIG. 2, the single A pattern 21 may be seen to have four quadrants. A first quadrant 23 has individual light scattering elements 25 spaced approximately 1 mm. apart in an array or cluster where the light scattering elements occupy intersections of an imaginary grid. The dimension of each light scattering element for use in testing semiconductor wafers is preferably on the order of a micrometer and specifically between 0.5 and 5.0 micrometers.

A second quadrant 27 has an increased areawise concentration of light scattering elements. Each individual light scattering element has the same dimension as in quadrant 23, but now the light scattering elements are grouped into clusters 29 of four, having an increased areawise density. The center-to-center spacing of each cluster is still approximately 1 mm.

The third quadrant 31 has a still higher areawise density of light scattering elements. While quadrant 27 had four elements per cluster, quadrant 31 has nine elements per cluster, each cluster being spaced, from center to center, by approximately 1 mm. The increased areawise density of light scattering elements, as represented by cluster 33, corresponds to the light which would be scattered from larger particles with reference either to clusters 29 in quadrant 27 or clusters 25 in quadrant 23.

A still higher density of light scattering elements is found in quadrant 35 where arrays of five by five light scattering elements, represented by cluster 37, is provided for simulating light scattered from large particles. If a surface scanner is detecting only light scattered from quadrant 35 of the A pattern, this means that only particles which scatter a corresponding amount of light are being seen. On the other hand, if light scattering elements 25 from quadrant 23 are seen, this means that particles that scatter a corresponding amount of light are being seen. The light scattering cross section of each light scattering element and cluster of elements may be determined experimentally. For example, light scattering elements in quadrant 23, if visible, might correspond to particles having a dimension on the order of one micrometer. On the other hand, if the only light scattering elements being seen are those in quadrant 35, then those surface particles also visible will have a dimension exceeding a predetermined amount, say 5 micrometers. The light scattering elements in quadrants 27 and 31 correspond to particles of intermediate sizes. The quadrant lines 30 are non-existant and merely provided for purposes of explanation. Each quadrant is completely filled by light scattering elements at a uniform spacing. This is indicated by jagged lines 32.

To review, the light scattering elements in quadrant 27 are clusters of four, formed by a two-by-two arrangement of elements, spaced at four micrometers between elements within a cluster. Quadrant 31 has clusters of nine formed by a three-by-three element array. Once again, the spacing between individual elements is 4 micrometers. The cluster of elements in quadrant 35 is formed by 25 elements, in a five-by-five array, with the spacing between individual elements being approximately 4 micrometers. The spacing between clusters is 1 mm., as previously mentioned. The size of each quadrant is a square 5 mm. on a side. Each array places elements at intersections on lines of an imaginary grid. These sizes are selected such that the size of a cluster is much less than the diameter of a beam. The beam itself is assumed to be Gaussian in shape. Any cluster of elements should be on the order of one-tenth or less of the diameter of the beam measured at the $1/e^2$ points. The spacing of clusters from center-to-centers must be such that the clusters are separately distinguishable. In practice this means that the clusters should be spaced at least ten times the $1/e^2$ beam diameter. The beam is typically a laser beam from a low power helium-neon laser.

The B pattern illustrated in FIG. 1 consists of light scattering elements disposed at intersections of a grid with lateral spacing between elements of approximately 10 micrometers and lengthwise spacing between elements of approximately 1 mm or 1,000 micrometers. This pattern is formed so that the closer spacing of elements at 10 micrometers will tend to form a series of transverse lines relative to a sweeping beam. It is expected that if the optical path between a test surface and a source is shortest at the center of the surface, the lines formed by the light scattering elements will be useful in defining areas of lesser instrument sensitivity if lines are seen to vanish.

The light scattering elements are formed by means of photolithography, as illustrated in FIG. 3. A substrate 41, which may be a semiconductor wafer, is coated with a thin layer 43 of oxide or nitride, typically about 1000 Angstroms thick. Other coatings may be used, but a coating substance must be inert to cleaning solvents. Light scattering elements are formed in the coating 43 by creating depressions 45, or islands or ridges, not shown. Such depressions may be made by the usual techniques known in the semiconductor industry. Typically, such techniques involve use of photoresist over the coating, making photographic patterns of the desired positions of light scattering elements of proper dimensions by means of photomasks and exposure to actinic radiation. Subsequently, regions are simultaneously etched out of the coating and the photoresist is removed. Depression 45 is shown to be a clean opening, the removed material being illustrated at a square 47 having an edge dimension 49 approximately 1.5 micrometers on a side. The depression need not extend to the substrate, but this is preferable because scattering will be increased from each depression. Alternatively, depressions may be formed by laser writing on a surface that can be pitted by the laser.

The test surface need not have a coating, but may be etched or pitted directly. The surface may be any smooth and polished material, not necessarily a wafer.

In operation, a scanning beam is directed over the surface in sweeps covering both the light scattering element patterns and blank spaces. A portion of the scattered light is collected in the manner set forth in U.S. Pat. No. 4,378,159. An electrical detector produces an electrical signal corresponding to the amount of received scattered light and converts the detected signal into a corresponding electrical signal. This electrical signal is synchronized with the position of the beam so that a comparison can be made between different areawise densities of light scattering elements and the random distribution of particles which will be seen in the spaces between patterns. This may be done visually by displaying the electrical signals on a cathode ray tube. The surface may be scanned in raster fashion so that the beam position will be readily known. The raster scan across the wafer may be correlated with the raster scan of the CRT. In this manner, the sensitivity of a surface scanner may be determined.

Important advantages of the present invention include: positive knowledge of instrument resolution with respect to particle or defect size and position and a manufacturing method which provides uniformity of the elements across the test surface.

We claim:

1. A device for calibration of light-scattering test instruments of the scanning type comprising,
   a substrate having a planar surface, and a plurality of identical microscopic light-scattering elements disposed on said surface, said elements grouped in grid-like clusters, the mutual spacing between elements in all clusters being equal to a first dimension, said clusters spaced apart from each other by a second dimension, the second dimension substantially exceeding the dimension of an illuminating beam, the first dimension being less than the dimension of an illuminating beam, some of said clusters grouped in a grid-like array of clusters having the same first element density, corresponding to a light scattering cross section associated with a flaw of a certain size on said surface, said array positioned near other grid-like arrays of clusters, the other arrays each having clusters with the same element density within each array, different arrays having mutually different element densities and different from said first element density, said other densities corresponding to light scattering cross sections associated with flaws of other sizes on said surface, the grouping of arrays on the surface forming a pattern, said pattern repeated over said surface, with each pattern contiguous with at least one other pattern.

2. The device of claim 1 further comprising, an "A" pattern of grid-like arrays of said microscopic light scattering elements, the A pattern having a rectangular grouping of said arrays of different densities, the A pattern repeated over said surface, and a "B" pattern of grid-like arrays of said microscopic light-scattering elements, the B pattern having a lengthwise spacing between said elements and a lateral spacing between said elements, said lateral spacing being close enough to form a series of lines, the repeated A patterns on the surface having intervening spaces between at least some of the A patterns, the B pattern repeated over said surface in a stripe intersecting the repeated A patterns.

3. The device of claim 2 wherein said A pattern comprises a pattern of four grid-like arrays, each array forming a quadrant of the A pattern.

4. The device of claim 1 wherein each array of the same density is spaced from each other array by a uniform distance.

5. The device of claim 1 wherein said elements have a surface dimension on the order of a micrometer.

6. The device of claim 1 wherein said elements have a surface dimension in the range of 0.3 micrometers to 5.0 micrometers.

* * * * *